United States Patent
Pustjens et al.

(10) Patent No.: US 10,759,745 B2
(45) Date of Patent: Sep. 1, 2020

(54) UREA PRODUCTION PROCESS AND PLANT

(71) Applicant: Stamicarbon B.V., Sittard (NL)

(72) Inventors: Ronny Albert Mathijs Pustjens, Sittard (NL); Johan Albert Arno Van Den Tillaart, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 16/186,410

(22) Filed: Nov. 9, 2018

(65) Prior Publication Data

US 2019/0185422 A1 Jun. 20, 2019

(30) Foreign Application Priority Data

Nov. 10, 2017 (EP) .................................... 17201121

(51) Int. Cl.
| | | |
|---|---|---|
| *C07C 273/04* | (2006.01) | |
| *B01D 5/00* | (2006.01) | |
| *C07C 273/16* | (2006.01) | |
| *B01J 19/00* | (2006.01) | |
| *C07C 273/14* | (2006.01) | |

(52) U.S. Cl.
CPC .............. *C07C 273/04* (2013.01); *B01D 5/00* (2013.01); *B01D 5/0054* (2013.01); *B01D 5/0057* (2013.01); *B01J 19/0053* (2013.01); *C07C 273/14* (2013.01); *C07C 273/16* (2013.01); *B01D 2257/406* (2013.01); *B01D 2257/504* (2013.01); *B01D 2257/70* (2013.01); *B01J 2219/0286* (2013.01)

(58) Field of Classification Search
None
See application file for complete search history.

(56) References Cited

U.S. PATENT DOCUMENTS 4,053,507 A * 10/1977 Inoue .................... C07C 273/04
564/71
2008/0286188 A1 11/2008 Meesen

FOREIGN PATENT DOCUMENTS

| CN | 103043809 | * | 4/2013 |
|---|---|---|---|
| EP | 2 801 396 | | 11/2014 |
| WO | WO-95/00674 | | 1/1995 |
| WO | WO-2013/165245 | | 11/2013 |
| WO | WO-2016/010432 | | 1/2016 |
| WO | WO-2016/153354 | | 9/2016 |
| WO | WO-2017/014632 | | 1/2017 |
| WO | WO-2019/093891 | | 5/2019 |

OTHER PUBLICATIONS

Ullmann's ("Urea" Ullmann's Encyclopedia of Industrial Chemistry, downloaded from https://onlinelibrary.wiley.com/doi/pdf/10.1002/14356007.a27_333.pub2 on Aug. 21, 2019, 2010, p. 657-695) (Year: 2010).*

(Continued)

*Primary Examiner* — Amy C Bonaparte
(74) *Attorney, Agent, or Firm* — Leason Ellis LLP (57) ABSTRACT

Processes and plants for the production of purified urea solution are described. In a described urea production process, urea is produced in a synthesis section without a high pressure stripper and the urea solution is subjected to purification after the recovery section, to give purified urea solution and off-gas. The purification comprises e.g. steam stripping.

18 Claims, 5 Drawing Sheets

(56) References Cited

OTHER PUBLICATIONS

Written Opinion of the International Searching Authority for PCT/NL2018/050747, dated May 16, 2019, 5 pages.
European Search Report for EP 17201121.5, dated May 15, 2018, 5 pages.
Ullman's Encyclopaedia of Industrial Chemistry, "Urea", Wiley-VCH Verlag GmbH, Weinheim, Germany (2012) vol. 37, p. 665.

* cited by examiner

UREA PRODUCTION PROCESS AND PLANT

CROSS-REFERENCE TO RELATED APPLICATIONS

This application claims benefit of European patent application No. 17201121.5 filed 10 Nov. 2017. The contents of the above patent application are incorporated by reference herein in their entirety.

The invention relates to the production of urea, in particular urea solutions, and especially to the production of purified urea solutions that are suitable to be used in NOx emission abatement systems, optionally after dilution with water. The invention in particular relates to the production of DEF (Diesel Exhaust Fluid), urea solutions that can be diluted with water to DEF, and other high purity urea solutions.

INTRODUCTION

The invention relates to a process and a plant for producing a urea solution. The urea product solution, optionally after water addition, is preferably suitable for use in a catalytic NOx abatement system, and is preferably a DEF solution. Accordingly, there is a requirement for very high purity. For example, DEF is used in vehicles with diesel engines for NOx emissions abatement. The composition of DEF for vehicles is standardized in ISO 22241-1:2006. DEF for vehicles has about 32.5 wt. % urea (i.e. essentially the eutectic composition) and also has very low impurities. In some embodiments, the product urea solution can also be used e.g. for NOx abatement in industrial plants and in ships and trains. For NOx abatement used in rail and marine applications, about 40 wt. % urea solution is used according to ISO 186111-1:2014. For NOx abatement for (fossil fuel) power plants, typically 50 wt. % urea solution is used. The term "DEF" as used in this application includes a urea solution that is suitable, adapted and/or identified for use in NOx abatement, e.g. according to any of said specifications.

For DEF, the concentration of urea is important in order to allow accurate dosing of the fluid to the catalyst. The low concentration of organic impurities is important to avoid clogging and coke formation on the catalyst. The very low concentration of inorganic impurities, in particular of heavy metals, is important because these impurities contribute to poisoning the SCR catalyst. The metals will accumulate on the catalyst and thereby reduce the lifetime. In the referenced specifications for DEF, the maximum limits for metal impurities are close to the typical achievable concentrations in urea streams obtained from a typical urea stripping plant. In particular during upset conditions or start-up conditions the amounts of metal in the urea solution from urea stripping plants exceed DEF specifications. In the case of a urea plant which is designed specifically for only DEF production and no solid urea production (e.g. a plant without urea solidification section) this may lead to significant amounts of material that is outside the product specifications and which cannot be handled in the plant (e.g. inside battery limits). ISO 22241-1:2006 specifies a limit for alkalinity as $NH_3$ of less than 0.2 wt. %; some commercial DEF solutions have an alkalinity as $NH_3$ as low as 200 ppm by weight. Low alkalinity is desirable in order to reduce the risk of corrosion of equipment in contact with the DEF solution.

A known preparation method for DEF is by dissolving commercially available solid urea (e.g. as used as fertilizers, such as prills and granules) in clean water while adding heat. However, a disadvantage is that purification for aldehydes is necessary because urea finishing (e.g. granulation) typically uses an aldehyde as solidification aid.

WO 2016/010432 describes a process for the preparation of a urea product suitable for being diluted with water so as to form DEF. The process involves flash crystallization at sub-atmospheric pressure and packaging the crystallized urea powder.

WO 2016/153354 describes a process for the integrated production of DEF and Urea Ammonium Nitrate (UAN) fertilizer.

US 2008/0286188 describes a process for the preparation of a urea-comprising aqueous stream, that is suitable for use in a unit for the reduction of $NO_x$ in combustion engine exhaust gases wherein the urea-comprising aqueous stream is separated directly from or after a recovery section in a urea production process and is thereafter diluted with water until the urea-comprising stream comprises 30-35 wt. % urea. In an embodiment, the urea-comprising stream is separated after a dissociation step that preferably involves steam stripping. US 2008/0286188 gives no information about the processing of the gaseous stream from the steam stripping step.

Urea plants usually comprise a urea synthesis section operating at high pressure, and a recovery section operating at medium and/or low pressure. If a solid urea product is made, the plant includes an evaporation section downstream of the recovery section. The evaporation section, e.g. comprising a vacuum evaporation step to evaporate water) is used to produce a urea melt with high urea content. The urea melt is solidified in a urea solidification unit such as a granulation unit or prilling tower.

The water vapour from the evaporation section is condensed and the condensate (which typically contains urea as impurity) is treated in a wastewater treatment section comprising, generally, a desorber and typically a hydrolysis unit. The treated condensate can be used e.g. as boiler feed water (BFW), or as scrubbing liquid e.g. for scrubbers provided in the recovery section.

For the high pressure synthesis section, three generations of plants are usually identified. Initially, urea was prepared from $CO_2$ and $NH_3$ in once-through reactors without recycle of $NH_3$ and $CO_2$. These were soon replaced by the total recycle process with a recycle for carbamate, which are now often called "conventional" total recycle plants to distinguish them from the later development of the third generation of plants that use a high pressure stripping process in the synthesis section. In high pressure (HP) stripping processes, the major part of the recycle of non-converted $NH_3$ and $CO_2$ (including ammonium carbamate) in the effluent of the high pressure reactor occurs via the gas phase using a high pressure stripper and a high pressure carbamate condenser.

The HP stripper uses e.g. a part of or the entire high pressure $CO_2$ feed as stripping agent to give high pressure stripped urea solution and a mixed gas stream that is condensed in the HP condenser.

The importance of conventional processes decreased rapidly as the processes employing HP strippers in the synthesis section were developed (Ullmann's Encyclopaedia, 2012, vol. 37, Urea, page 665).

The present invention provides a process and plant for the production of purified urea solutions, in particular as discussed above, and in particular of sufficient purity to be used as DEF, preferably with relatively simple equipment and low capital expenditure.

SUMMARY

The invention pertains to a process for the production of a purified urea solution that is preferably suitable for use in NOx abatement, in particular for use as diesel exhaust fluid (DEF) or dilution to DEF, the process comprising:

A) reacting $CO_2$ and $NH_3$ under urea synthesis conditions in a urea synthesis reactor operating at high pressure, to give a urea synthesis stream containing urea, $NH_3$, $CO_2$ and an amount of carbamate, B) expanding the urea synthesis stream in a recovery section thereby reducing the pressure, wherein the urea synthesis stream that is expanded comprises at least 90 wt. % of said amount of carbamate,
and heating at least part of the expanded urea synthesis stream in one or more dissociation units at medium and/or low pressure, to give an aqueous urea stream and a recovery section vapour containing $NH_3$ and $CO_2$, C) subjecting in a purification section at least part of the aqueous urea stream to purification, wherein the purification is preferably performed by stripping, more preferably by low pressure (LP) stripping, and/or wherein the purification preferably yields a urea solution with an alkalinity as $NH_3$ of less than 0.2 wt. % when at 32.5 wt. % urea, to remove (excess) ammonia, giving a purified urea solution and a purification section off-gas containing water and ammonia, D) optionally diluting at least part of the purified urea solution and/or the aqueous urea stream to be purified with water to obtain a target concentration of urea, E) wherein the purification section off-gas is condensed to give purification section condensate and said purification section condensate is recycled to said urea synthesis reactor.

The process typically does not include HP stripping of non-converted $NH_3$ and $CO_2$ which results in the feature of B that the urea synthesis stream that is expanded contains at least 90 wt % of the initial carbamate in the urea synthesis stream. In urea plants with HP strippers, a large portion of carbamate is removed and sent to a carbamate condenser before the stream containing urea is expanded under reduced pressure.

The invention also pertains to a plant for the production of a purified urea solution which urea solution is preferably suitable for use in NOx abatement systems, in particular for use as diesel exhaust fluid (DEF) or dilution to DEF, the plant comprising:

A) a urea synthesis section comprising a high pressure urea synthesis reactor having an inlet for $CO_2$ and an inlet for $NH_3$, wherein $CO_2$ and $NH_3$ are reacted under urea synthesis conditions to form a urea synthesis stream comprising urea, water, and ammonium carbamate, B) a recovery section wherein the urea synthesis stream is heated at reduced pressure, giving an aqueous urea stream and a recovery section vapour comprising $CO_2$ and $NH_3$, and wherein preferably said recovery section vapour is condensed in said recovery section to give carbamate and ammonia, preferably with separate condensers for ammonia and for carbamate, C) a purification section wherein the aqueous urea stream is treated, preferably is purified, more preferably is stripped, in a purification section treatment unit to remove (excess) ammonia, giving a purified urea stream and a purification section off-gas, D) optionally a urea dilution section, wherein the purified urea stream and/or the aqueous urea stream is diluted with water,
wherein the plant comprises a recycle conduit for carbamate from the recovery section to the urea synthesis section and preferably a separate second recycle conduit for ammonia from the recovery section to the urea synthesis section, wherein the purification section further comprises a purification section condenser for condensing the purification section off-gas to purification section condensate, and wherein the plant comprises a liquid flow connection for purification section condensate from said purification section condenser to said urea synthesis reactor.

The plant, in some embodiments, does not include a high pressure stripper in the synthesis section for recovery of unreacted $NH_3$ and $CO_2$.

DETAILED DESCRIPTION

The present invention is in part based on the surprising result that expanding the urea synthesis stream to reduced pressure without subjecting it to high pressure stripping results in improved purity of the urea solution ultimately produced. The invention is also based in part on the judicious insight that a low $NH_3$ content of the purified urea solution can be achieved by using a purification step which gives, besides the purified urea solution, an off-gas that contains water and ammonia, and wherein the off-gas is condensed and the condensate is recycled to the urea synthesis. The condensate is in particular recycled by liquid flow, such that the liquid water fraction of the condensate is supplied to the urea synthesis and ends up in the product urea solution. Hence, the condensate does not need to be processed in a wastewater treatment section. At the same time the ammonia in the condensate is reacted in the urea synthesis reactor. Furthermore, surprisingly, a relatively high urea conversion can still be achieved in the urea synthesis reactor, despite the water recycle from the purification section, by virtue of the synthesis section being preferably of the type without a high pressure stripper. In a preferred embodiment passivation air is omitted, giving a smaller water recycle stream from scrubbers for inert gases of the urea plant.

As used herein, for urea solutions and process medium streams, high pressure (HP) is for example 120 to 300 bar; medium pressure (MP) is for example 10 to 70 bar (including intermediate pressure of 30 to 70 bar), in particular 15 to 25 bar; and low pressure (LP) is for example 0 to 10 bar, in particular 1 to 8 bar or 2 to 5 bar, or 3 to 10 bar or 3 to 5 bar.

Step A comprises urea synthesis in a urea synthesis reactor by reacting $CO_2$ and $NH_3$ to form ammonium carbamate that is dehydrated to urea and water. The reactor is operated preferably 150 to 250 bar, for instance 180 to 250 bar and/or e.g. at a temperature higher than 190° C. These pressures and temperatures are higher than typically used for urea plants with high pressure strippers. The reactor typically receives $NH_3$ feed and $CO_2$ feed, both at high pressure and typically with separate inlets. The $CO_2$ feed optionally contains passivation air for preventing corrosion in the reactor; however in preferred embodiments very little (e.g. less than 0.2 vol %, preferably less than 0.1 vol. % (e.g. less than 0.10 vol. %), for example less than 0.050 vol. %) or no passivation air is used. For the reactor, the molar $NH_3$:$CO_2$ ratio (N/C ratio) is typically 2.0-6.0, preferably 2.7-5.0 and for example 3.3 to 5.0, 3.5 to 5.0, or 4.0 to 5.0, wherein the ratio reflects the composition of the so-called initial mixture before urea production, consisting only of $NH_3$, $CO_2$ and $H_2O$. The molar $H_2O$: $CO_2$ ratio is for instance 0.10-2.0, for example 0.50-1.0, also as initial mixture before urea production. For instance the water recycle from the purification section causes a relatively higher molar $H_2O$: $CO_2$ ratio. An N/C ratio of 3.5-5.0 is higher than the N/C ratio of 3:1 typically used for a synthesis section according to the Stamicarbon $CO_2$ stripping process. An N/C ratio higher than 3:1 can be advantageously used because the pressure minimum (or temperature maximum) shifts toward higher $NH_3$:$CO_2$ ratios as the amount of solvent (water and urea) increases in the reactor.

The $CO_2$ feed typically also contains inert gases (i.e. gases which do not react in the urea synthesis reactor), such as e.g. $H_2$ from the $CO_2$ production process or $N_2$ from passivation air. The reactor also receives a carbamate recycle stream from the recovery section, as carbamate solution which also contains water. The reactor has an outlet for urea synthesis stream, for instance at the top, and for instance as only outlet. The urea synthesis stream at the outlet of the urea synthesis reactor contains urea, water, and also unreacted $NH_3$, $CO_2$ and carbamate, as well as typically some inert gas. The urea synthesis stream typically contains liquid and vapour.

The process of the invention typically does not involve stripping at high pressure of the urea synthesis stream.

The process of the invention typically does not involve subjecting the entire urea synthesis stream, or the entire liquid part thereof, to heating and/or gas/liquid separation at high pressure, e.g. at the reactor operating pressure or above 120 bar and does not involve high pressure stripping such as ammonia stripping, thermal stripping (self-stripping), and $CO_2$ stripping. These three types of HP stripping are well known in the art and are discussed e.g. in Ullmann's Encyclopaedia, chapter Urea. A synthesis section with thermal stripping often has a urea reactor with an inlet for a mixture of carbamate and $NH_3$ connected to an ejector driven by the $NH_3$ feed to supply carbamate recycle into the reactor. In some embodiments, the process does not involve introducing $CO_2$ into the high pressure urea synthesis stream at a location that is both downstream of the reactor outlet and outside of the reactor ($CO_2$ feed is typically introduced in the reactor in the present invention). However, in some alternative embodiments, a part of the urea synthesis stream is subjected to high pressure stripping and a part is not. In some embodiments, at least a part of the urea synthesis stream is not subjected to high pressure stripping. In some other embodiments, where particular features are included, such as wherein a cyclone separator is included, the entire urea synthesis stream is subjected to high pressure stripping, however for instance with a very low amount of strip gas.

Preferably, at least 85%, preferably at least 90%, more preferably at least 95% of the fresh $CO_2$ is added directly into the reactor, i.e. is introduced as gaseous stream into the reactor. The remaining fresh $CO_2$, if any, is for example added downstream of the synthesis section, e.g. to correct the N/C ratio for optimal condensation of ammonia as carbamate. Herein, "fresh" refers to a stream received from battery limit.

Furthermore, especially for the plant of the invention, the urea synthesis section typically does not contain a HP stripper, in particular not a high pressure $CO_2$ stripper. High pressure strippers (as typically not used in the present plant) are for instance shell-and-tube heat exchangers configured for flow of urea synthesis stream in the pipes and steam on the shell side.

Moreover, the urea synthesis section typically does not contain a HP carbamate condenser unit, such as with a U-shaped tube bundle, the HP condenser having an outlet for liquid connected by piping to an inlet of the urea synthesis reactor.

Step B comprises reducing the pressure, usually with an expansion valve, thereby expanding the urea synthesis stream, or at least a part of said stream that is not subjected to high pressure stripping. Typically the pressure is reduced by at least 10 bar or at least 20 bar, and typically to medium pressure. The urea synthesis stream that is expanded comprises typically at least 90 wt. % of the amount of carbamate present at the outlet of the urea synthesis reactor, and typically all the unreacted carbamate, because the process preferably does not contain separating carbamate from the urea synthesis stream between said reactor outlet and said expansion step.

Step B further comprises heating at least a part of the expanded urea synthesis stream, typically after gas/liquid separation, to dissociate unreacted carbamate, in one or more dissociation units. Generally, in step B, the heating is by indirect heat exchange.

The dissociation unit for example comprises a rectifying column and a decomposer, wherein the decomposer comprises a heat exchanger for indirect heat exchanging with steam. The rectification column provides for counter-current contact of the vapour from the decomposer and the colder (upstream) urea solution such that water vapour is condensed from the vapour. The decomposer is arranged e.g. below the rectification column.

The dissociation units operate at medium pressure (MP) and/or low pressure (LP). Preferably, an MP dissociation unit and a downstream LP dissociation unit are used in series. Preferably the LP unit operates at between 3 and 7 bar. The heated urea synthesis stream is subjected to gas/liquid separation. This yields an aqueous urea stream and a recovery section vapour containing $NH_3$ and $CO_2$. In an embodiment, heat integration may be achieved by using recovery section vapour (containing gaseous $CO_2$, $NH_3$ and water vapour) from an MP dissociation unit to provide at least part of or all of the heat to the decomposer of the LP dissociation unit, e.g. by indirect heat exchange between that MP recovery section vapour and urea solution supplied to the decomposer of the LP dissociation unit. In particular a condenser for the MP recovery section vapour can be integrated with such a decomposer, such that condensation of the MP recovery section vapour occurs in indirect heat exchange contact with the carbamate decomposition in the LP dissociation unit.

The dissociation unit or the most upstream one of the dissociation units of step B has an inlet for receiving (at least part of) the expanded urea synthesis stream. In some embodiments, the molar ratio $NH_3$:$CO_2$ of the urea synthesis stream (including both liquid and any gas) at this inlet is substantially the same as at the outlet of the reactor, e.g. with a deviation of less than 10% relative to that ratio at the reactor outlet, i.e. less than 10% numerically, e.g. with outlet N/C ratio of 4.0, in the range 4.4-3.6 at said inlet.

Each dissociation unit is preferably configured for gas/liquid separation and preferably comprises an outlet for gas and a separate outlet of the urea-containing liquid.

The process typically furthermore comprises condensing recovery section vapour in a recovery section condenser, and gas/liquid separation, to give a liquid carbamate recycle stream, and non-condensed gases. This condenser operates at lower pressure than the urea synthesis reactor, and typically at the same pressure as the respective dissociation unit, e.g. at MP or LP. The liquid carbamate recycle stream is supplied to the urea synthesis reactor, typically using a pump.

The non-condensed gases typically comprise inert gases, as well as $NH_3$ and $CO_2$. The non-condensed gases are usually scrubbed, usually in counter-current flow, with a scrubbing liquid in one or more scrubbers, to give scrubbed gas and a liquid stream. The scrubbed gas can, optionally after further treatment, be vented to the environment. The liquid stream containing carbamate is, optionally as purge stream, recycled to the urea synthesis reactor, e.g. through the condenser.

The scrubbing liquid typically comprises water and typically make-up water is supplied to at least one of the scrubbers of the recovery section. In prior art urea plants, the make-up water is usually obtained as cleaned condensate from the waste water treatment section. In the present invention, the make-up water is for instance supplied from another plant, such as an upstream gasification and/or ammonia plant. For the production of purified urea solution with 32.5 wt. %-50 wt. % urea, the addition of water from battery limit is required anyway because the urea formation reaction gives a 1:1 molar ratio urea and water, i.e. 77 wt. % urea.

Elegantly, make-up water used as (part of) scrubbing liquid in an absorber can be used as carbamate solvent in the condenser if (a purge of) spent scrubbing liquid is sent to the condenser.

In a preferred embodiment, step B comprises MP and LP dissociation units in series. Hence, step B preferably comprises: B1) expanding the urea synthesis stream to medium pressure, optionally gas/liquid separation, and heating at least part of the urea synthesis stream at MP to give a MP recovery section vapour and a MP aqueous urea solution, and B2) expanding the MP aqueous urea solution to low pressure, and heating the expanded aqueous urea solution at low pressure to give a LP recovery section vapour and a LP second aqueous urea solution.

In this case, the recycling of carbamate of step B preferably comprises a) condensing said MP recovery section vapour at medium pressure in a medium pressure condenser to give a MP carbamate stream, and b) condensing said LP recovery section vapour at low pressure in a low pressure condenser to give a LP carbamate stream.

In some embodiments, the plant has a recycle conduit for carbamate and a separate recycle conduit for ammonia from the recovery section to the HP reactor, in particular from an MP condenser to the reactor. Preferably, the non-condensed gas from the MP condenser is condensed in an ammonia condenser and sent to the HP reactor separately from the MP carbamate stream. In this way excess $NH_3$ due to a relatively high N/C ratio in the reactor can be accommodated. The carbamate recycle may include free $NH_3$ and preferably has an N/C ratio of 2.0-2.5, e.g. 2.0-2.3. If the gas supplied to the (MP) condenser has a higher N/C ratio, the excess $NH_3$ is preferably separately condensed and recycled to urea synthesis.

Step B yields an aqueous urea stream that usually contains ammonia, e.g. unreacted ammonia (in particular in view of the relatively high N/C ratio) and/or ammonia formed by decomposition of ammonium carbamate in step B. The aqueous urea stream yielded in step B usually contains less than 2.0 wt. % or less than 1.0 wt. % ammonium carbamate, and e.g. more than 0.20 wt. % residual ammonium carbamate, in particular based on total weight of the stream.

Step C is used in order to produce the purified urea solution, e.g. the desired DEF or DEF precursor solution.

The process comprises step C of subjecting the aqueous urea stream obtained from step B to purification in a purification section, giving a purified urea solution stream and purification section off-gas. The purification preferably removes ammonia from the urea solution. In particular the purification preferably removes excess ammonia, i.e. ammonia above the desired level, in particular above the desired alkalinity as $NH_3$ level. This removal ensures that the purified solution has sufficiently low alkalinity. Low alkalinity is important to avoid the risk of corrosion of equipment in contact with the DEF solution. Lower $NH_3$ content of the DEF solution advantageously reduces ammonia smell. The removal of ammonia refers to transfer of $NH_3$ from the liquid phase to the gas phase; the $NH_3$ in the liquid phase results e.g. at least in part from decomposition of ammonium carbamate in the liquid phase during step B and/or step C, and/or as unreacted ammonia from step A.

The purification, preferably stripping, is preferably such that the purified solution, as obtained by said purification has an alkalinity as $NH_3$ of less than 0.20 wt. %, less than 1000 ppm, less than 500 ppm, or less than 200 ppm, all by weight, when at 32.5 wt. % urea, i.e. the alkalinity converted on the basis of water added or removed as necessary to have 32.5 wt. % urea, in other words said alkalinity levels are on the basis of 32.5 wt. % urea solution. Lower alkalinity is preferred.

In some embodiments, the purification involves reducing the alkalinity as $NH_3$ of a urea solution to be purified, by at least 50% or at least 90% or at least 99%, as relative percentage of the initial alkalinity as $NH_3$ value, by transfer of a corresponding amount of ammonia (in any form in the solution) to the gas phase. The purified solution having such low alkalinity typically has an urea content of less than 95 wt. % or less than 90 wt. % (e.g. is not a urea melt), and/or typically has a urea content of more than 20 wt. % or more than 30 wt. %, such as a urea content in the range of 20-95 wt. %. In the embodiment wherein the purification yields urea solution with an alkalinity as $NH_3$ of less than 0.2 wt. %, the initial urea solution can already have an alkalinity below the specified level, in which case the alkalinity as $NH_3$ is further reduced by the purification.

In some embodiments, the purification, such as stripping, in particular the low pressure stripping, involves dissociation of ammonium carbamate to $NH_3$ and $CO_2$, and transfer of this formed $NH_3$ from the liquid phase to the gas phase to remove the $NH_3$ from the solution, typically together with transfer of free $NH_3$ from the liquid phase to the gas phase. Typically with such dissociation the alkalinity as well as the carbonate content (as $CO_2$) is reduced, for instance to a carbonate content (as $CO_2$) of said purified solution of less than 0.5 wt. % or less than 0.2 wt. %, or to less than 1000 ppm or less than 500 ppm by weight, on the basis of 32.5 wt. % urea solution.

The purification for example involves pressure reduction (i.e. reduction of the absolute pressure), heating, stripping, and combinations of these. In some embodiments the purification involves heating and/or pressure reduction without stripping.

The purification preferably comprises low pressure stripping. Stripping allows for reducing the purification temperature thereby advantageously reducing biuret formation. The stripping preferably involves contacting the urea solution in counter current flow with a gaseous stream. The gaseous stream typically has a lower partial vapour pressure of $NH_3$ than the urea solution that is in contact with the gas. The stripping preferably involves steam stripping. Air stripping can also be used. The steam stripping preferably involves contacting the aqueous urea solution in counter current flow with steam. The steam is preferably supplied from battery limit. Alternatively, the steam can be raised by evaporation of water from urea solution, e.g. downstream of the purification step, such as with reboiling. The stripping is preferably carried out at a pressure of less than 3 bar. An advantage of steam stripping is stripping effect by the low partial ammonia vapour pressure, preferably in addition maintaining a high vapor pressure of water to reduce water evaporation. Some advantages of direct steam stripping with externally supplied steam are that dilution of the urea solution with water is useful for making DEF, and that downstream reboiling of urea solution causing biuret formation can be avoided.

The purification is for instance based on heating the solution, to cause ammonia evaporation, and preferably also involves reducing the partial $NH_3$ pressure of the gas phase by stripping and/or reducing the absolute pressure. As a result of the heating and preferred (absolute) pressure reduction, water is also evaporated. The purification section off-gas may comprise predominantly water vapour, e.g. more than 50 wt. %, more than 70 wt. %, more than 90 wt. %, or more than 99 wt. % water, and e.g. from 0.5 wt. % and/or up to 5 wt. % $NH_3$. In some embodiments, the purification section off-gas and/or purification section condensate comprise $NH_3$ in an amount corresponding at least 0.010 wt. % and/or max. 5.0 wt. % of the urea solution received by the purification section. The purification is section is preferably based on direct heat exchange and comprises preferably contacting, e.g. mixing, the urea solution with a fluid stream having a higher temperature than the urea solution.

The purification for instance comprises steam stripping of the aqueous urea solution. Steam stripping typically involves direct injection of steam in the aqueous urea stream, typically in counter-current flow, such as with liquid flowing down and steam flowing up. The stream of steam preferably comprises at least 90 wt. % $H_2O$, more preferably at least 95 wt. % $H_2O$. The steam is preferably supplied from battery limit, e.g. from another plant such as from a utility plant. The pressure of the steam as injected is for instance 1 to 30 bar (absolute), preferably 2 to 15, typically 2 to 6 bar (absolute). The purification step, may be conducted by low pressure (LP) stripping, and may include steam stripping. Low pressure stripping is carried out at less than 10 bar, or less than 5 bar, less than 3.0 bar, less than 2.0 bar, or less than 1.5 bar (absolute), or at 0.10-1.1 bar (absolute), e.g. at less than 1.0 bar absolute, for example at 0.010 to 0.50 bar, or at 0.4 to 0.5 bar (absolute). Such operating pressures are in particular used for the steam stripper. The process comprises e.g. expanding the urea solution at between 3 and 7 bar obtained from step B to the pressures of the stripping step at e.g. less than 1.5 bar (absolute). The steam stripper for step C is for example a vessel configured for counter-current flow of steam and liquid, having a liquid inlet at the top and liquid outlet at the bottom, and steam inlet in the bottom part and gas outlet at the top. The vessel for instance comprises trays and/or a packing.

The preferred low operating (absolute) pressure of the purification section advantageously allows for purification by ammonia evaporation at lower temperatures, and hence reduced biuret formation. Hence, in a preferred embodiment, step C comprises expanding the aqueous urea solution obtained from step B, preferably the second aqueous urea solution obtained from LP dissociation (B2), to the operating pressure of the purification section, and subsequently steam stripping the expanded aqueous urea stream, wherein the steam stripping involves direct injection of steam into the expanded aqueous urea stream.

The process involves condensing the purification section off-gas to purification section condensate. The present invention provides an elegant way of disposing of the purification section condensate, which contains ammonia, without using a waste water treatment section, by recycling the purification section condensate back to the urea synthesis reactor, preferably by liquid flow. In this way, the ammonia does not end up in the purified urea product solution and is reacted to urea in the synthesis section. By the recycle, the water fraction of the condensate is also supplied to the urea rector.

The recycle of the purification section condensate to the synthesis section is preferably by liquid flow, i.e. through one or more flows of liquids. Accordingly, the plant preferably comprises a liquid flow connection from the purification section condenser directly or indirectly to the synthesis section.

The condensation step may be carried out as absorption of the ammonia in an aqueous stream, e.g. make-up water, with gas/liquid separation to give a condensate stream and a second off-gas.

The process generally involves condensation of the recovery section vapour to give a carbamate stream in a recovery section condenser, and recycle of a carbamate stream to the urea synthesis reactor. Preferably, the purification section condensate is sent to a recovery section condenser. In this way, the purification section condensate recycle stream is combined with the carbamate recycle stream of the recovery section. In this way, elegantly, steam used in the purification step C, and any water used for absorbing ammonia, may provide for at least part of the condensation water required in the condensers of the recovery section for preventing carbamate crystallization. In some embodiments, the carbamate recycle stream is passed through a gas/liquid separator to separate ammonia gas from carbamate solution, the ammonia gas can be recycled separately to the reactor optionally through an $NH_3$ feed compressor.

The purification section condenser may involve gas/liquid separation giving the purification section condensate stream and a second off-gas. Preferably at least part of said second off-gas is supplied to a condenser of the recovery section. Preferably, the second off-gas is supplied to a scrubber, e.g. using an ejector using steam.

The scrubber for the second off-gas is preferably the scrubber to which non-condensed gases of at least one recovery section condenser for vapour from a dissociation unit are sent to, optionally through an additional condenser. The scrubber is preferably used for scrubbing with scrubbing liquid, e.g. make-up water, to give scrubbed gas (which is typically vented) and spent scrubbing liquid. A purge stream of the spent scrubbing liquid is for instance supplied to the additional condenser and then to the condenser for vapour from a dissociation unit.

In the embodiment with MP and LP dissociation units in series, the second off-gas is preferably supplied to the LP scrubber, more preferably with an additional LP condenser between the LP condenser for condensing the LP recovery section vapour and said LP scrubber. The additional LP condenser receives non-condensed gas from the LP condenser and has a gas outlet to the LP scrubber.

The purified urea solution is a urea solution with for example 50-70 wt. % urea. The purified urea solution from step C is in some embodiments obtained as product as DEF precursor solution and can be packaged and/or stored. In some embodiments, the water content of the purified urea solution obtained from step C is not more than 10 percent point lower (arithmetic difference) than the water content as received by the purification section, or not more than 5 percent point lower and/or the purification section off-gas contains water vapor in an amount of less than 10 wt. % or less than 5 wt. % of the aqueous urea solution received by the purification section. Hence, step C usually does not involve extensive evaporation of water.

The process optionally comprises step D of diluting the purified urea solution with water, i.e. by adding water, to a desired target urea concentration, e.g. to about 32.5 wt. % urea for DEF according to ISO 22241-1:2006, such as to 30-35 wt. % urea, to about 40 wt. % urea solution according to ISO 186111-1:2014, such as to 33-45 wt. % urea, or e.g. to about 50 wt. % urea solution for NOx abatement in industrial plants, such as to 45-55 wt. %, or diluting to any other desired target value. The optional dilution step is e.g. carried out in a urea dilution section, which is e.g. a mixer, a mixing vessel, or a tube or duct where water is added to the urea solution. The dilution step gives e.g. a urea solution product stream.

The dilution water is e.g. demineralized water (e.g. de-ionized water) from a utility plant, or e.g. purified process condensate e.g. from another plant (such as an upstream gasification or ammonia plant), or from e.g. the urea process if the urea plant includes a waste water treatment section. The dilution water can also be e.g. steam condensate from the steam system of the plant or from another (utility) plant. In principle, dilution water can also (and alternatively) be added upstream in the process, hence both in addition to a dilution downstream of said purification or alternatively to (instead to) such dilution downstream of said purification. Dilution upstream of the purification step can be useful for preventing crystallization of the urea during the purification step and for preventing crystallization between step B and step C, e.g. in a urea storage tank between the recovery section and the purification section. Hence, in some embodiments the aqueous urea stream is diluted, by adding water, prior to being purified in step C, this dilution can also be carried out in the dilution section. The dilution section may contain two dilution units, e.g. one unit upstream of the purification section and one unit downstream of said section.

The purified solution from step C and optional step D has low impurities. Preferably, the impurities are in agreement with envisaged use as DEF or for the dilution to DEF, particularly DEF in compliance with ISO 22241-1:2006 (i.e. with 32.5 wt. % urea) and/or ISO 186111-1:2014. Hence, in some embodiments biuret is max. 0.3 wt. % and/or $NH_3$ is max 0.2 wt. %, e.g. alkalinity as $NH_3$ is max 0.2 wt. %. Preferably carbonate as $CO_2$ is 0.2 wt. % max. Furthermore, preferably, aldehydes are max 5 ppm (by weight) and/or insoluble matter is max 20 ppm (by weight). Preferably, $PO_4$, Ca, Fe, Al, Mg, Na and K are each max 0.5 ppm. Cu, Zn, Cr and Ni are preferably each max 0.2 ppm (all ppm by weight). For DEF precursor solution, the impurities are preferably such that said impurities are obtained after dilution by adding water to the urea content of the DEF specification (e.g. at 31.8 wt. % urea). Hence, in some embodiments, step C is treatment, preferably stripping, yielding a urea solution with biuret max. 0.3 wt. % and/or $NH_3$ max. 0.2 wt. %. In some embodiments step C is treatment, preferably stripping, yielding a urea solution with biuret max. 0.3 wt. % and/or $NH_3$ is max. 0.2 wt. % when at 32.5 wt. % urea, i.e. when the urea content is set at 32.5 wt. % by adding or removing water as necessary.

Surprisingly it was found that by using the plant and process of the invention the (heavy) metal impurities and the biuret levels are significantly lower than in the plants of the prior art. Without wishing to be bound by theory, the inventors believe that although the reactor in the present process is operated at a higher pressure and/or higher temperature than reactors in a typical urea plant of the stripping type, the lower number of high pressure units and/or the lower surface area in contact with corrosive carbamate solution leads to a significantly lower concentration of metals in the final DEF solution. The lower biuret level is provided by the different process conditions compared to a stripping plant, in particular the higher N/C ratio, such that more $NH_3$ present in the recovery section. A lower biuret level such as max 0.20 wt. % or max 0.10 wt. % or max 0.05 wt. % in the purified solution (e.g. on the basis of 32.5 wt. % urea), indicates higher product quality as more urea is available for NOx abatement by the (catalysed) reaction of urea with NOx.

The solution, optionally after the dilution step, e.g. DEF and/or DEF precursor solution, is obtained as product. Hence, the solution is withdrawn as product at the battery limit. The solution is e.g. stored in a storage tank. The product solution is for instance metered into batches, e.g. from the storage tank. The batches are e.g. packaged, e.g. in vessels or containers, which is preferred to maintain purity, and/or supplied in transportation units such as vehicles or ships. The product solution for instance contains about 30 to about 50 wt. % urea, or about 32.5 wt. % to about 40 wt. %, or about 40 to about 50 wt. %. The plant is preferably provided with a purified urea solution storage tank and a unit for metering purified urea solution into batches, and preferably with a transport line for from the storage tank to a product dispensing unit for dispensing the purified urea solution product into a container and/or into a movable transportation unit such as a ship, train or vehicle.

In an interesting embodiment, the urea plant does not include a urea solidification unit such as a prilling tower or granulation unit. Furthermore, in some embodiments the urea plant does not involve an evaporation section for concentrating urea by water evaporation, in particular not a vacuum evaporator for water evaporation from the urea solution obtained from the recovery section. The (vacuum) evaporation section is usually arranged in known plants between the recovery section and a solidification section so as to provide a urea melt with e.g. more than 90 wt. % urea by water evaporation. In known urea plants, the water evaporated in the evaporation section is not recycled to the high pressure synthesis section, since the water is essentially a by-product of urea synthesis. This is a difference with the water vapour in the gas stream from a dissociator of a recovery section, which is generally recycled to the synthesis section as part of the carbamate recycle stream and helps to prevent carbamate crystallization.

Known urea plants typically include a waste water treatment section that is used for treating condensate from condensation of the vapour from the evaporation section. In an example known waste water treatment section, urea in the condensate is hydrolysed into $NH_3$ and $CO_2$ which are stripped of with steam and the purified process condensate is purged. Only purified condensate can be released into the environment under many environmental regulations.

In some embodiments of the invention, the plant does not include a waste water treatment (WWT) section. In some embodiments the plant does not include a WWT section comprising a desorbing unit and/or a hydrolysis unit. The aqueous purification section condensate is recycled to the urea synthesis reactor.

Preferably, the purification section comprises a purification section treatment unit and a condenser. The treatment unit is preferably a steam stripper, more preferably a low pressure steam stripper. A steam stripper has a supply member and/or an inlet for steam, which is typically connected to a steam source, e.g. at battery limit, such as a utility plant. Preferably, the steam stripper comprises a stripping column comprising a cyclone separator at the top, a liquid distribution tray, and a packed bed. The packed bed preferably comprises Pall rings and is typically arranged below the liquid distribution tray. In operation, a two phase fluid of expanded aqueous urea stream enters the cyclone separator; gas leaves at the top, liquid flows down from the cyclone separator on e.g. a liquid distribution tray, which distributes the liquid over the packed bed. Gas rises up, e.g. through chimneys on the liquid distribution tray.

Preferably, the purification section is configured for operating at low pressure, e.g. at up to 1.5 bar absolute, preferably below 1.0 bar absolute. Preferably the purification section comprises an ejector, blower, and/or vacuum pump for maintaining a low pressure, e.g. below 1.0 bar absolute, preferably an ejector.

Preferably the plant comprises a recycle conduit for carbamate from the recovery section to the urea synthesis section and preferably a separate second recycle conduit for ammonia from the recovery section to the urea synthesis section. The separate recycle conduit for ammonia (e.g. optionally through an ammonia receiving vessel) can be used for recycle of excess ammonia (compared to carbamate recycle) at lower temperature than the carbamate recycle. The excess ammonia can be provided by a relatively high N/C ratio of the synthesis section. Preferably the recovery section comprises a condenser for condensing recovery section vapour to give carbamate, and preferably a second separate condenser to give ammonia. The second condenser preferably receives non-condensed gas from the recovery section condenser wherein carbamate is formed.

Preferably, the plant comprises a gas flow line from the purification section to an off-gas condenser, a liquid flow line from the off-gas condenser to said condenser of the recovery section having an inlet for recovery section vapour, and a liquid flow line from said condenser of the recovery section to said urea synthesis reactor. Hence the ammonia from the purification section off-gas is preferably recycled to the reactor through the recovery section.

The reactor is preferably a vertical reactor. The reactor preferably has an inlet for $CO_2$ feed and preferably has an inlet for compressed $NH_3$, these inlets can optionally be combined.

The urea synthesis reactor preferably comprises a ferritic-austenitic duplex stainless steel, e.g. is at least in part made of such steel, for instance as described in WO 95/00674, and e.g. as sold under the trademark Safurex®, and e.g. as registered as ASME Code 2295-3 and e.g. as UNS 532906; or as described in WO 2017/014632. For example the ferritic-austenitic duplex stainless steel has a chromium content of between 28 and 35 wt. % and a nickel content of between 3 and 10 wt. %, preferably with a composition: C: maximum 0.05 wt. %; Si: maximum 0.8 wt. %; Mn: 0.3-4.0 wt. %; Cr: 28-35 wt. %; Ni: 3-10 wt. %; Mo: 1.0-4.0 wt. %; N: 0.2-0.6 wt. %; Cu: maximum 1.0 wt. %; W: maximum 2.0 wt. %; S: maximum 0.01 wt. %; Ce: maximum 0.2 wt. %; the balance consisting of Fe and common impurities and additives, e.g. balance Fe and unavoidable impurities, wherein the ferrite is 30 to 70 vol %. A further suitable duplex stainless steel is DP28W (TM) which is also designated by ASME Code 2496-1 and by UNS S32808. Such a duplex stainless steel has preferably the following composition (% by mass): C: 0.03 or less; Si: 0.5 or less; Mn: 2 or less; P: 0.04 or less; S: 0.003 or less, Cr: 26 or more, but less than 28, Ni: 6-10, Mo: 0.2-1.7, W: more than 2, but no more than 3, N: more than 0.3, but no more than 0.4, the balance being Fe and impurities, wherein the content of Cu as an impurity is not more than 0.3%, preferably a steel as described in EP 2801396.

The amount of passivation air, if used, is preferably 0-0.6 wt. %, preferably 0-0.3 wt. %, more preferably 0-0.1 wt. % of the $CO_2$ feed. If passivation air or oxygen is used, this can be introduced e.g. through the $NH_3$ feed and/or $CO_2$ feed. In some embodiments, no passivation air is added to the $CO_2$ feed, especially if the reactor comprises corrosion resistant materials such as said steel alloys. Such low amount of passivation air provides for less inert gas in the urea synthesis stream and may provide for a lower scrubber load and accordingly the relatively low amount of spent scrubbing liquid can be supplied to the urea synthesis reactor, e.g. with streams 533 and 515 in FIGS. 1a-1d.

The invention is suitable for modifying existing plants as well as for grassroots plants (i.e. newly built plants). The invention is suitable for all sizes of urea plants, in attractive embodiments the plant and/or process is a small scale urea plant or process, such as with a capacity of e.g. 50-1000 MTPD (metric ton per day), e.g. a capacity of 50-500 MTPD. In some embodiments, the invention is implemented as total recycle plants of the type without HP stripper with capacity of 50-1000 MTPD or 50-500 MTPD. The invention also pertains to a method of constructing such a plant, preferably including newly constructing the sections A, B and C. The inventive plant provides for relatively lower capital expenditure and lower construction space requirements.

The urea plant typically receives $NH_3$ feed from an ammonia plant, and the ammonia plant is preferably provided with an ammonia storage tank and a unit for metering ammonia product to be used as fertilizer into batches, and preferably with a transport line for ammonia from the ammonia storage tank to a product dispensing unit for dispensing the ammonia fertilizer product into a container and/or into a movable transportation unit such as a ship, train or vehicle. For a plant comprising an ammonia plant and a urea plant, wherein the urea plant is as described, the ammonia plant preferably has a switchable ammonia transport line to the $NH_3$ feed of the urea plant such that the ammonia product can go to the ammonia product dispensing unit and the urea plant, in a variable ratio, e.g. variable such that 0 to 100% of the ammonia product goes to the ammonia product dispensing unit.

Advantageously, the synthesis section can have the reactor as the only high pressure unit, reducing capital expenditure to a stripping type process. The absence of a high pressure stripper (and the heating in such a stripper, in particular in case of ammonia strippers and thermal strippers, and also in case of $CO_2$ strippers) results in lower biuret content in the urea solution which is especially important in DEF. By omitting stripping (and the HP carbamate condenser), the urea solution has a lower metal content and the process involves less corrosive process conditions. In particular the intermediate product ammonium carbamate is extremely corrosive, at high temperature such as in a high pressure stripper. In particular, in a stripping plant, the reactor can operate at e.g. about 185° C. (compared to e.g. 195° C. for a reactor of a conventional urea plant), but the peak temperatures at the top of the HP stripper are e.g. at 210-220° C. Furthermore, high pressure strippers are typically shell-and-tube heat exchangers with urea solution in the pipes and steam on the shell side, and in a high pressure stripper the amount of metal surface in contact with ammonium carbamate solution is high due the large number of pipes. The lower metal content is in particular advantageous in embodiments of the plant of the invention without a urea solidification section and/or that are specifically designed for producing only purified urea solution.

The lower metal content of the urea synthesis solution and urea product solution is important for use as DEF and as reductant in NOx abatement systems, because these systems contain an (expensive) catalyst for selective catalytic reduction. Metal content of the urea solution decreases life time of the catalyst because of metal accumulation. The low metal content (i.e. metal concentration) of the purified urea solution provides hence for a longer lifetime of the catalyst.

In a particular embodiment, no or substantially no passivation air is used, e.g. less than 0.05 wt. % or less than 0.010 wt. %, or even less than 0.0010 wt. % oxygen in the $CO_2$ feed. In known urea plants of the ($CO_2$) stripping type, even when using a corrosion resistant material, for example Safurex® for the high pressure synthesis equipment, some passivation air (e.g. about 0.3 wt. % oxygen in the $CO_2$ feed) is typically used in view of the harsh conditions in particular the high pressure stripper. The process medium (containing ammonium carbamate) is usually more corrosive at the conditions in (the top part of) the HP stripper than at the conditions in a HP synthesis reactor, e.g. due to higher temperature. By using a synthesis section that does not include a high pressure stripper, the passivation air is optionally eliminated. This provides the advantage that a step of hydrogen removal from the $CO_2$ feed can be omitted. Because the $CO_2$ feed is typically produced from natural gas in a gasification plant, the feed contains $H_2$ that needs to be removed if passivation air is used to reduce the risk that the off-gas from the urea synthesis reactor, which oxygen and hydrogen, is explosive. Hence, in embodiments wherein no passivation air is used, the $CO_2$ feed may contain more than 20 ppm or more than 100 ppm by weight $H_2$. A further advantage that amounts of inert gases (including $N_2$) are lower because no passivation air is added, thereby reducing the load of the scrubbers.

The invention also pertains to a process for the production of a purified urea solution comprising:

A) reacting $CO_2$ and $NH_3$ under urea synthesis conditions in a urea synthesis reactor operating at high pressure, to give a urea synthesis stream containing urea, $NH_3$, $CO_2$ and an amount of carbamate, typically also water, wherein urea synthesis is carried out in a high pressure synthesis section that does not include a high pressure stripper and/or in a reactor receiving $CO_2$ and $NH_3$, B) expanding the urea synthesis stream in a recovery section thereby reducing the pressure, wherein preferably the urea synthesis stream that is expanded comprises at least 90 wt. % of said amount of carbamate, and heating at least part of the expanded urea synthesis stream in one or more dissociation units at medium and/or low pressure, to give an aqueous urea stream and a recovery section vapour containing $NH_3$ and $CO_2$, C) subjecting in a purification section at least part of the aqueous urea stream to purification to remove (excess) ammonia, giving a purified urea solution and a purification section off-gas containing water and ammonia, D) optionally diluting at least part of the purified urea solution and/or the aqueous urea stream with water to obtain a target concentration of urea, E) wherein the purification section off-gas is condensed to give purification section condensate and said purification section condensate is recycled to said urea synthesis reactor; furthermore preferably having the features as described. In some embodiments, the purification of step C is stripping and/or gives urea solution with an alkalinity as $NH_3$ of less than 0.20 wt. % when at 32.5 wt. % urea; with the further preferred features for the stripping, dilution, and purification as described herein.

DETAILED DESCRIPTION OF THE DRAWINGS

FIGS. 1a-1d illustrates an example embodiment of the process and plant which does not limit the invention or the claims.

Liquid ammonia 109 is supplied from battery limit, to the ammonia receiving vessel V106 through heater E100. With a booster pump P101 the ammonia 109X, 110A is pumped to the high pressure ammonia pump P102 and compressed to about 200 bar. Seal water of the pump P102 may leak into the process stream, illustrated as stream 1204. The ammonia 111, 112 is then sent, via a pre-heater E103 to the mixing compartment of the high pressure reactor R201.

Carbon dioxide 103 from battery limit is supplied, optionally together with a small amount of air 104, e.g. via blower S101 as gas 105 to the carbon dioxide compressor K102 before it is compressed to about 200 bar, optionally also giving water condensate 106 to remove water droplets and CO2 blow-off stream 108. A hydrogen converter R101 is optionally provided, e.g. after the compressor K102. In this optional converter R101 the hydrogen, present in the carbon dioxide 117, is removed by catalytic combustion. A portion of the supplied air is used for this catalytic combustion while the remainder is used to passivate the equipment of the synthesis section and so prevent corrosion. The dehydrogenated carbon dioxide 118, is also introduced into the mixing compartment of the high pressure urea synthesis reactor R201. In some embodiments, no passivation air is used and the converter 101 is omitted.

The dehydration of ammonium carbamate into urea and water takes place in the high-pressure reactor R201. The top temperature of the reactor is controlled at about 200° C. The remaining heat, required to meet this top temperature, is controlled by heating in heater E103 the ammonia before it is supplied to the mixing compartment.

The urea synthesis stream (202, 212) comprising non-condensed vapour together with the urea solution leaving the urea reactor R201 at the top is expanded to MP, about 20 bar (501, 511) with an expansion valve X1. As a result of the expansion a portion of the carbamate, left in the solution, decomposes and vaporizes to give part of vapour 505. The remaining urea solution 512 is distributed into a rectifying column C501 e.g. onto a bed of Pall rings. The urea/carbamate solution 513 is sent from the bottom of the rectifying column to a decomposer E501 where its temperature is raised to about 160° C. in order to decompose the remaining carbamate in the urea solution. The heat required for this decomposition is supplied by steam. In the separator, at the bottom part of the rectifying column, the gas phase 502 is separated from the liquid phase 514. The gases 502 are sent to the rectifying part C501 of the rectifying column where the gases 503 are cooled by the colder urea/carbamate solution 512. This causes a portion of the water vapour contained in the gases to condense. The gases 504, 505 leaving the rectifying column are introduced (as gases 508X, 521X) into the bottom part of the medium-pressure carbamate condenser E503 where they are condensed as carbamate for a large part. The heat of condensation is dissipated into a tempered cooling water system. The non-condensed ammonia rich vapour 521 from the flash vessel V501 of the medium-pressure carbamate condenser is sent to a washing column C502. In this washing column C502 the ammonia is separated from the carbon dioxide water mixture by adding ammonia containing liquid (110B, 113 and 114) from vessel V106, e.g. as reflux. The liquid stream 515 leaves the washing column C502 via the bottom and is added to the gas stream 505. The ammonia vapour 523, containing only traces of carbon dioxide, leaves the washing column C502 overheads and is condensed in ammonia condenser E101. The condensed ammonia 530 is transferred to the ammonia receiving vessel V106 and in this way recycled to the reactor R201 separately from the carbamate recycle stream 510.

From the condenser E101 the non-condensed gas 524, mainly inert gas, is supplied to the atmospheric absorber C102 together with gas 109A from vessel V106 and is washed with demineralized water 1205. The non-condensed gas 526 is vented. The liquid stream 531 from the bottom of atmospheric absorber C102 is via pump P103 sent to cooler E102 and the cooled stream 532 is for a part 533A used as scrubbing liquid in atmospheric absorber C102 and for the remaining purge part 533 used as scrubbing liquid in washing column C502.

The urea solution 514 leaving the medium-pressure decomposer is expanded to LP, about 4 bar, using an expansion valve X2. As a result of the expansion a portion of the carbamate, left in the solution, decomposes and vaporizes to give a two phase fluid stream 301, 311 supplied to the top of the low pressure rectifying column C303. Gas/liquid separation at the top of the low pressure rectifying column C303 gives urea solution 312 and part of vapour 305.

The remaining liquid 312 is distributed in a low-pressure rectifying column C303, e.g. onto a bed of Pall rings. The urea/carbamate solution 313 is sent from the bottom of the rectifying column to a heater E302 where its temperature is raised to about 135° C. in order to decompose the remaining carbamate. The heat required for the decomposition is supplied by low-pressure steam. In the separator, at the bottom part of the rectifying column, the gas phase 302 is separated from the liquid phase 314. The gases 302 are sent to the rectifying part of the rectifying column where the gas 303, 304 is cooled by the colder urea/carbamate solution 312. This causes a portion of the water vapour contained in the gases to condense. The gases 304, 305 leaving the rectifying column are introduced into the bottom part of the low-pressure carbamate condenser E303 where they are condensed almost completely. The heat of condensation is dissipated into a tempered cooling water system. The non-condensed gases 321 are separated from the solution 308 in vessel V301. The formed carbamate solution 308, 310 is conveyed to the medium-pressure carbamate condenser E503 in the medium-pressure recirculation section using pump P302 and through the washing column C502.

The urea solution 314 leaves the bottom of the rectifying column, is adiabatically expanded using a valve X3 to atmospheric pressure (e.g. 1-2 bar), and is discharged to an atmospheric flash vessel S304. Due to the adiabatic expansion and the flash, a part of the water and almost all of the ammonia, carbon dioxide are liberated from the liquid. Urea solution 319 at the exit of flash vessel S304 has a higher urea concentration and a lower temperature than urea solution 314. The liberated vapour 701 leaves the atmospheric flash S304 at the top and is sent together with the non-condensed vapour 321 from the low pressure carbamate condenser to an atmospheric flash tank condenser E311 where it is condensed almost completely. The formed lean carbamate condensate 722, 723 in the atmospheric flash tank condenser E311 is conveyed with pump P308 to the low-pressure carbamate condenser E303. The urea solution 319 is introduced in the purification section.

The urea solution 319 contains about 59 wt. % urea and 1-2 wt. % ammonia, and has a pressure of about 1.1 bar. The urea solution 319 is pumped with pump P350, expanded with expansion valve X4, and stripped in a steam stripping column C350 by counter-current contacting with low-pressure steam 922 at about 0.47 bar (abs).

The off-gas 353 of the stripping column C350, optionally with some leakage air 785, is sent to a vacuum condenser E701 to which also e.g. demineralized water 1206 is supplied. The condensate 712 of condenser E701 is sent to the low-pressure carbamate condenser E303 using pump P701. In this way, the aqueous condensate 712 that also contains ammonia is disposed of, in particular by in effect recycle of both the water and the ammonia to reactor R201.

The packed bed of the stripping column C350, consisting of metal Pall rings, provides for a good liquid-gas contact between the urea solution 319 and the low pressure steam 922. Via the bottom of the column 350, the stripped liquid 352 flows to the optional DEF mixing vessel V350. The mixing vessel is operated at atmospheric conditions, therefore in this example about 8 meters of static height between the bottom of the stripping column C350 and the mixing vessel is used for proper discharge of the liquid from the column.

In the mixing vessel V350 the stripped urea solution is optionally diluted with demineralized water 1203 to the desired concentration (e.g. 32.5, 40, or about 50 wt. % urea). The amount of water is determined based on the urea concentration of the urea solution in the mixing vessel, which can e.g. be measured. Mixing and cooling occurs via circulation of the diluted urea solution 354, 355 over the vessel V350 and a circulation cooler E350, using a circulation pump P351, and withdrawing a purge product solution 356. This circulation cooler E350 is operated with cooling water, cooling the urea solution in the mixing section to about 30° C.

The non-condensed gas 705 from the atmospheric flash tank condenser E311 is sent to a washing column C305 where it is washed with demineralized water 1202 to give cleaned gas 341 that is vented and a liquid stream 342 from which a part 344 is recycled with pump P309 and cooler E312 and the remaining purge stream 343 is sent to atmospheric flash tank condenser E311. Non-condensed gas 703 from condenser E701 is sent with ejector J701 using low pressure steam 921 to the washing column C305.

In the illustrated example embodiment of column C350, the top of the column C350 includes a gas-liquid cyclone separator C350A which separates the two-phase flow of the expanded liquid. Via a cyclone separator the gas 353 leaves the top of the column C350, while the liquid flows down on a liquid distribution tray C350B. The liquid distributor tray C350A distributes the process liquid equally over the packed bed C350C via liquid holes. The liquid distribution tray has for instance chimneys to ensure that the rising gas from the bottom of the column C350 can flow to the top of the column. From the flash vessel V501, the carbamate recycle 508 is sent to pump P501 and compressed carbamate recycle 510 is sent to reactor R201. Stream 1201 indicates possible leakage of sealing water. For FIGS. 1*a*-1*d*, some features are explicitly identified as optional, other features can also be optional.

Figure 1:
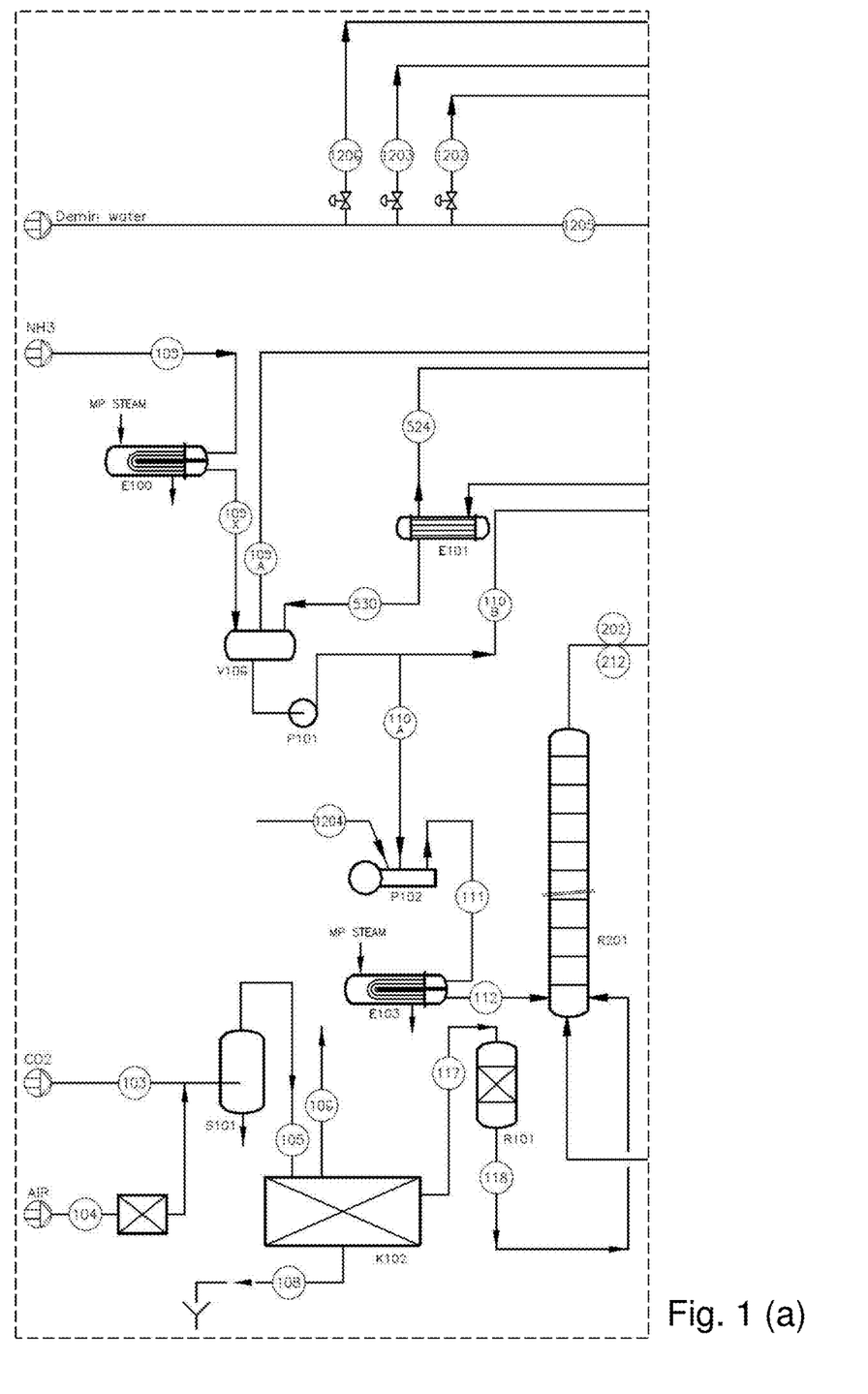
FIGS. 1a-1d show an example process scheme according to the invention.
Figure 2:
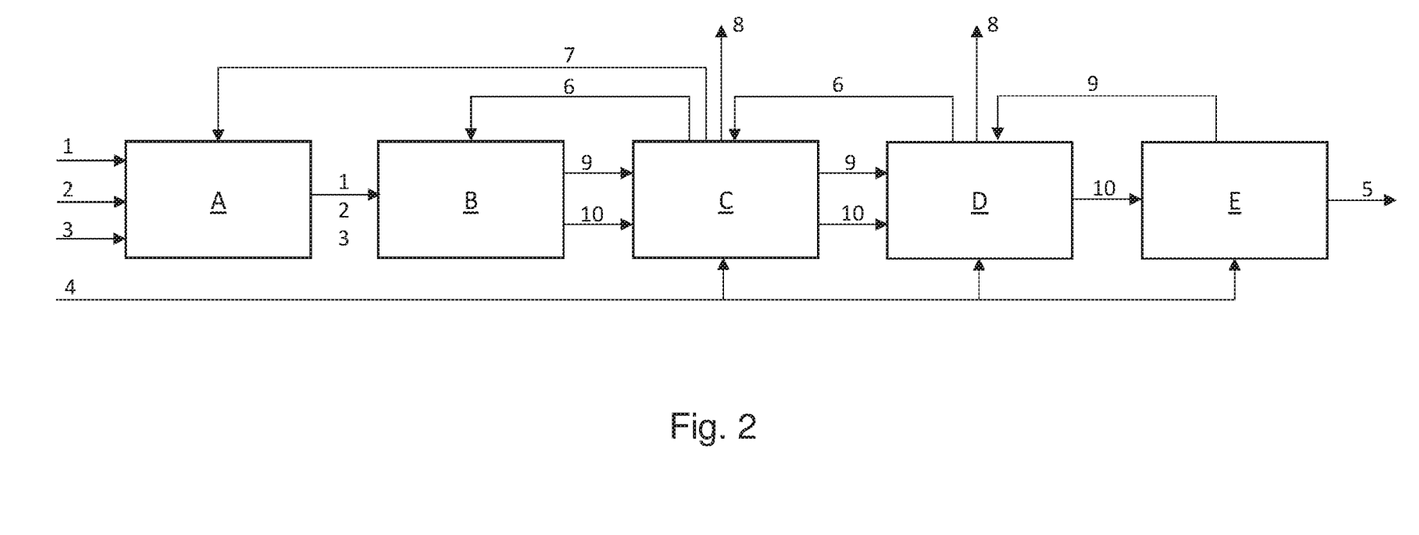
FIG. 2 shows a schematic diagram of an example process according to the invention.

FIG. 2 shows a further example process scheme which illustrates but does not limit the invention or the claims. In compression section A (optionally including hydrogen removal), $NH_3$ feed 1 and $CO_2$ feed 2 are compressed to high pressure and optionally air 3 is added to the $CO_2$ feed for passivation. In some embodiments, passivation air 3 and hydrogen removal are not used. Urea is formed in HP synthesis section B, and the synthesis stream contains a component 9 containing $NH_3$, $CO_2$, water and inert gases (gases not participating in urea formation reactions), and a component 10 comprising aqueous urea solution. The synthesis stream containing the mixed components 9 and 10 is sent to MP recovery section C. In MP recovery section C, part of the $NH_3$ and $CO_2$ is removed, and sent as carbamate recycle stream 6 to synthesis section B. Excess ammonia is provided as recycle stream 7 to the synthesis section B through compression section A, typically separately from the carbamate recycle stream 6. Inert gases 8 are vented after scrubbing in sections C and D. A stream comprising components 9 and 10 is sent to the LP recovery section D. A carbamate recycle 6 is sent from section D to section C. The aqueous urea solution 10 is purified in purification section E, e.g. with steam stripping using steam from water 4. The urea solution 10 is optionally diluted by water addition in section E, to give purified urea solution 5. Stream 9 from section E to section D contains some $NH_3$ and typically majority water. Water 4 is supplied from an external source typically to unit E, and typically also to scrubbers in sections C and D.

As used herein, phrases such as "typically", "generally", "in particular" and "usually" indicate features that are not essential for the invention. Reference numerals to the drawings are used for convenience and do not limit the invention or the claims. The process as described is preferably carried out in the plant as described. The plant as described is preferably configured for the process as described.

The invention claimed is:

1. A process for the production of a purified urea solution optionally after dilution, the process comprising:
   A) reacting $CO_2$ and $NH_3$ under urea synthesis conditions in a urea synthesis reactor operating at high pressure, to give a urea synthesis stream containing urea, $NH_3$, $CO_2$ and an amount of ammonium carbamate,
   B) expanding the urea synthesis stream in a recovery section thereby reducing the pressure, wherein the urea synthesis stream that is expanded comprises at least 90 wt. % of said amount of ammonium carbamate, and heating at least part of the expanded urea synthesis stream in one or more dissociation units at medium and/or low pressure, to give an aqueous urea stream and a recovery section vapour containing $NH_3$ and $CO_2$,
   C) subjecting in a purification section at least part of the aqueous urea stream to purification, wherein the purification is stripping to remove ammonia and/or wherein the purification yields a urea solution with an alkalinity as $NH_3$ of less than 0.2 wt. % when the alkalinity is converted on the basis of water added or removed as necessary to have 32.5 wt. % urea, giving a purified urea solution and a purification section off-gas containing water and ammonia,
   D) optionally diluting at least part of i) the purified urea solution from step C) and/or ii) the aqueous urea stream from step B) prior to the stream's purification in step C), with water to obtain a target concentration of urea in said solution and/or stream,
   E) wherein the purification section comprises a purification section condenser and the purification section off-gas is condensed in the purification section condenser to give purification section condensate and said purification section condensate is recycled to said urea synthesis reactor.

2. A process according to claim 1, wherein the purification section condensate is supplied by liquid flow to the urea synthesis reactor, and wherein the purification is low pressure steam stripping and involves contacting the aqueous urea stream in counter current flow with steam at a pressure of less than 3 bar.

3. A process according to claim 1, further comprising:
   (a) condensing the recovery section vapour to give a liquid ammonium carbamate recycle stream in a recovery section condenser, wherein said condenser operates at a lower pressure than said urea synthesis reactor,
   (b) supplying the ammonium carbamate recycle stream to the urea synthesis reactor,
   (c) and supplying said purification section condensate to said recovery section condenser before said purification section condensate is recycled to said urea synthesis reactor in step E.

4. A process according to claim 3, further comprising a step of supplying non-condensed gases from the recovery section condenser, to a scrubbing step with a scrubbing liquid in a scrubber to give a scrubbed gas and a spent scrubbing liquid, and wherein the purification section condenser gives a second off-gas and the process further comprises supplying the second off-gas from the purification section condenser to said scrubber.

5. A process according to claim 1, wherein step B comprises
   B1) expanding the urea synthesis stream to medium pressure, and heating at least part of the urea synthesis stream at medium pressure to give a MP recovery section vapour and a MP aqueous urea solution, and
   B2) expanding the MP aqueous urea solution to low pressure, and heating the expanded aqueous urea stream at low pressure to give a LP recovery section vapour and a LP aqueous urea solution.

6. A process according to claim 1, wherein step A involves supplying a fresh $CO_2$ feed into the reactor, wherein at least 85% of the fresh $CO_2$ feed is added directly into the reactor.

7. A process according to claim 1, wherein said step C further comprises expanding said aqueous urea stream, to the operating pressure of the purification section to provide an expanded aqueous urea stream, and wherein step C comprises steam stripping the expanded aqueous urea stream, wherein the steam stripping involves direct injection of steam in the expanded aqueous urea stream.

8. A process according to claim 7, wherein the steam stripping is carried out at 0.010 to 1.5 bar absolute in a stripping column with a cyclone separator at the top of the column, a liquid distribution tray and a packed bed, wherein gas is separated from the expanded aqueous urea stream in the cyclone separator, the gas exits through an outlet at the top, liquid flows down from the cyclone separator onto the liquid distribution tray, and the liquid distribution tray distributes the liquid over the packed bed.

9. A process according to claim 1, wherein no passivation air is used.

10. The process according to claim 1, wherein the purified urea solution is suitable for use in NOx abatement.

11. The process according to claim 1, wherein the purified urea solution is suitable for use as diesel exhaust fluid (DEF) optionally after dilution.

12. The process according to claim 7, wherein the purification section operating pressure is in the range of 0.010 to 1.5 bar absolute.

13. A process according to claim 1, wherein step A involves supplying a $CO_2$ feed into the reactor and wherein the $CO_2$ feed contains less than 0.05 wt. % oxygen.

14. The process according to claim 1, wherein the high pressure is a pressure between 120 and 300 bar.

15. The process according to claim 1, wherein the medium pressure is a pressure between 10 and 70 bar.

16. The process according to claim 15, wherein the medium pressure is a pressure between 15 and 25 bar.

17. The process according to claim 1, wherein the low pressure is a pressure between 0 and 10 bar.

18. The process according to claim 17, wherein the low pressure is a pressure between 3 and 5 bar.

* * * * *